(12) United States Patent
Harfouche

(10) Patent No.: US 11,147,475 B2
(45) Date of Patent: Oct. 19, 2021

(54) DEVICE FOR MEASURING THE CIRCUMFERENCE OF AN OBJECT

(71) Applicant: Just A New Health, Beauvechain (BE)

(72) Inventor: Joseph Harfouche, Forest (BE)

(73) Assignee: Just A New Health, Beauvechain (BE)

( * ) Notice: Subject to any disclaimer, the term of this patent is extended or adjusted under 35 U.S.C. 154(b) by 276 days.

(21) Appl. No.: 16/349,368

(22) PCT Filed: Nov. 14, 2017

(86) PCT No.: PCT/EP2017/079198
§ 371 (c)(1),
(2) Date: May 13, 2019

(87) PCT Pub. No.: WO2018/091462
PCT Pub. Date: May 24, 2018

(65) Prior Publication Data
US 2019/0365284 A1  Dec. 5, 2019

(30) Foreign Application Priority Data

Nov. 15, 2016 (BE) .............................. 20160005858

(51) Int. Cl.
*G01B 3/1005* (2020.01)
*G01B 3/1041* (2020.01)
(Continued)

(52) U.S. Cl.
CPC .......... *A61B 5/1075* (2013.01); *A61B 5/1072* (2013.01); *G01B 3/008* (2013.01);
(Continued)

(58) Field of Classification Search
CPC .... G01B 3/008; G01B 3/1005; G01B 3/1041; G01B 3/1061; G01B 3/1084;
(Continued)

(56) References Cited

U.S. PATENT DOCUMENTS

| 2,129,582 A | * | 9/1938 | Johansson | G01B 3/1084 |
| | | | | 33/555.4 |
| 3,832,780 A | * | 9/1974 | Lewis | A41H 1/02 |
| | | | | 33/2 R |

(Continued)

FOREIGN PATENT DOCUMENTS

GB  2452256 A * 3/2009 ............. A61B 5/107

*Primary Examiner* — Yaritza Guadalupe-Mccall
(74) *Attorney, Agent, or Firm* — Hanley, Flight & Zimmerman, LLC

(57) ABSTRACT

The present invention relates to a device for measuring an object, comprising a winder of a measuring element arranged to form a loop about the said object, which has at least one wall and an exit opening arranged to allow the exit of at least one unwound portion of the said measuring element, which is defined between the said exit opening and a distal end of the said measuring element, which is provided with a connecting element that abuts against the said exit opening, and a connecting means being located at a distance d from the said exit opening, characterised in that the said connecting means is located on the said at least one wall, is adjacent to the said exit opening, is presented in the form of a protrusion which extends towards the said distal end, and is arranged to receive the said connecting element in a stationary manner.

18 Claims, 3 Drawing Sheets

(51) Int. Cl.
*A61B 5/107* (2006.01)
*G01B 3/00* (2006.01)
*G01B 3/1061* (2020.01)
*G01B 3/1084* (2020.01)
*G01B 3/1069* (2020.01)
*G01B 3/1094* (2020.01)

(52) U.S. Cl.
CPC ......... *G01B 3/1005* (2013.01); *G01B 3/1041* (2013.01); *G01B 3/1061* (2013.01); *G01B 3/1084* (2013.01); *G01B 3/1069* (2020.01); *G01B 3/1094* (2020.01); *G01B 2003/103* (2013.01)

(58) Field of Classification Search
CPC ............... G01B 3/1069; G01B 3/1094; G01B 2003/103; G01B 2003/1053; G01B 3/1056; G01B 2003/1028; G01B 2003/1079; A61B 5/1075; A61B 5/1072; A61B 5/6824; A61B 5/6831; A61B 5/6828
USPC .......................................... 33/755–771, 514.2
See application file for complete search history.

(56) References Cited

U.S. PATENT DOCUMENTS

| 3,918,166 | A | * | 11/1975 | Mason | G01B 3/1084 33/514.2 |
| 4,974,331 | A | * | 12/1990 | Watterson | A41H 1/02 33/15 |
| 5,062,215 | A | * | 11/1991 | Schlitt | G01B 3/1003 33/755 |
| 5,193,287 | A | * | 3/1993 | Coulter | A61B 5/107 33/511 |
| 5,367,785 | A | * | 11/1994 | Benarroch | E05B 67/006 33/755 |
| 5,371,949 | A | * | 12/1994 | Delaurier | A63C 19/06 33/1 G |
| 5,613,302 | A | * | 3/1997 | Berman | G01B 5/025 33/514.2 |
| 5,732,475 | A | * | 3/1998 | Sacks | A61B 5/1073 33/512 |
| 6,640,460 | B1 | * | 11/2003 | Nabarro | A41C 5/00 33/759 |
| 6,817,110 | B2 | * | 11/2004 | Bohnengel | G01B 3/1056 33/511 |
| 7,146,743 | B2 | * | 12/2006 | Oura | G01D 5/363 33/756 |
| 9,377,288 | B2 | * | 6/2016 | DeLucia | G01N 33/0098 |
| 9,858,611 | B2 | * | 1/2018 | Cooper | A41H 1/10 |
| 2002/0184779 | A1 | * | 12/2002 | Bohnengel | G01B 3/1084 33/555.4 |
| 2011/0258869 | A1 | * | 10/2011 | Bittkowski | A61B 5/107 33/512 |
| 2012/0266479 | A1 | * | 10/2012 | Park | G01B 5/0035 33/712 |
| 2014/0196301 | A1 | * | 7/2014 | Towns | A43D 1/08 33/769 |
| 2016/0113549 | A1 | * | 4/2016 | Harfouche | A61B 5/415 600/587 |
| 2019/0365284 | A1 | * | 12/2019 | Harfouche | A61B 5/6831 |

\* cited by examiner

DEVICE FOR MEASURING THE CIRCUMFERENCE OF AN OBJECT

This patent arises from the U.S. national stage of International Patent Application Serial No. PCT/EP2017/079198, having an international filing date of Nov. 14, 2017, and claims benefit of Belgian Patent Application No. 2016/5858, filed on Nov. 15, 2016, which are hereby incorporated by reference in their entireties for all purposes.

The present invention relates to a device for measuring the circumference of an object, in particular the circumference of a limb, comprising:

a winder of a flexible measuring element arranged to be affixed and form a loop around the said object, in particular around the said limb, when the said measuring element is in a measuring position, the said reel having at least one wall and an exit opening arranged to allow the exit of at least one unwound portion of the said measuring element, the said at least one unwound portion of the said measuring element being defined between the said exit opening and a distal end of the said measuring element, the said distal end of the said measuring element being equipped with a connecting element that abuts against the said exit opening, when the said measuring element is in the rest position, and connecting means of the said connecting element of the said distal end of the said measuring element, the said connecting means being located at a distance d from the said exit opening and the said connecting means being less than or equal to 4 cm, preferably less than or equal to 3 cm, preferably less than or equal to 2 cm, and more preferably less than or equal to 1 cm, and most preferably equal to zero.

Such a device is used in particular for measuring the circumference of the arms, thighs and legs of a patient, the measuring element typically having graduations. To measure the circumference of a limb, it is first necessary to unwind at least a portion of the measuring element from the winder outlet and then place this unwound portion around the limb, this prior to or after the distal end of the unwound measuring element is connected to a connecting means. Once this connection is established, the operator must ensure that the unwound portion of the measuring element follows the contours of the limb and a reading of the limb circumference can then be achieved using the graduations.

Note that the devices of the prior art generally have a curvature facilitating the placing of the device against a limb to conform to the shape. However, each device has its own curvature and is therefore more or less suited to a given limb of a specific diameter. But, when the curvature of the limb is different and especially less than that of the measuring device according to the state of the art, measurement errors of a few centimetres and a significant loss of accuracy are noted.

Circumference measurements are also currently performed with simple measuring devices corresponding to tape measures. However, the use of a tape measure is particularly restrictive because the operator has to hold it in place such that it overlaps at least partially in order to determine a circumference and he needs to be careful not to exert too much traction on the tape measure, and must do all this while remaining motionless so as not to distort the measurement.

A measurement of the circumference of limbs such as an arm or leg is especially recommended in the assessment and monitoring of the physiotherapy treatment, for example for the treatment of lymphedema, i.e. the swelling of a part of the body following an accumulation of lymphatic fluid in the interstitial tissue. These swellings mainly affect the upper and lower limbs such as, for example, the fingers, toes, arms, feet, legs, thighs and hands, but can also occur in other parts of the body such as the neck, abdomen, back or breasts.

In order to determine to what extent the lymphedema (primary or secondary) must be treated, it is necessary to monitor changes. For example, if we consider secondary lymphedema of the upper limbs, clinical practice guidelines for the care and treatment of breast cancer (Clinical practice guidelines for the care and treatment of breast cancer, Canadian Medical Association Journal) recommends measuring the brachial circumference at four points: the metacarpal-phalangeal joints, wrists, 10 cm below and 15 cm above the lateral epicondyles (elbow). It is considered that a difference of more than 2 cm in the circumference between two measurements at one of these four measurement points justifies the treatment of lymphedema. A difference of more than 2 cm in the circumference between a limb (e.g. the right arm) with lymphedema and a corresponding limb (e.g. the left arm) not having lymphedema also indicates that it is appropriate to treat this swelling.

It is therefore necessary to have a measuring device or instrument that can measure the circumference of limbs occasionally and at the same place in order to be able to decide whether treatment of lymphedema is applicable or not. It is particularly necessary to have a measurement tool that allows for accurate and reliable measurement since the margin of error must be small and only of a few millimetres, preferably in the range of less than 5 millimetres and more preferably in the range of less than 2 millimetres.

A measurement of the circumference of limbs is also indicated to record a decrease in the volume of skeletal muscles and monitor any changes. Such a decrease in muscle volume (or loss of muscle mass) may, for example, be due to muscle wasting (atrophy and/or disappearance of the striated muscle fibre), sarcopenia (geriatric syndrome) or myopathy (neuro-muscular disease). These conditions require monitoring and especially physiotherapy treatment, in which an accurate measurement of the circumference of the limb with the muscle in question is essential. Again, the change in the circumference of the limb can be monitored by comparing two measurements taken at the same location after a predetermined period of time or by comparing the circumferences of a "healthy" limb and a corresponding limb affected by a decrease in muscle volume (loss of muscle mass).

A measurement of the circumference of limbs is also indicated to record a decrease in volume when following a diet and during anti-cellulite treatments, during which the limb is expected to become thinner.

A measurement of the circumference of limbs is also indicated to record a change in volume when following a body-building programme where an increase in muscle volume is expected or desired.

Finally, a measurement of the circumference of limbs is also indicated to monitor the growth of infants, which involves taking circumference measurements of very thin and very small limbs, where no measurement error can be tolerated.

It is understood that any other condition or pathology involving a change in the circumference of a limb falls within the scope of the present invention.

Unfortunately, with a measuring device such as the one described above and used currently, it appears that the measurements are accurate and reliable only for certain objects/limbs of average circumferences. On the contrary, these measurements are totally biased when objects/limbs have very small circumferences (e.g. fingers, toes, wrists and ankles) or, conversely, very large circumferences (e.g. the abdomen). For example, this totally biased measurement problem is encountered while measuring the circumference of very thin limbs of infants or while measuring the circumference of fingers.

Another problem encountered with such a device, as is currently used, is that the shape and curvature of the objects/limbs have a direct impact on measurement accuracy. For example, while a correct and accurate measurement can be noted at the wrist of an adult when the measuring device is placed flat just behind the head of the ulna (like a watch), this will not be the case if the same measuring device is offset by 90° to the right or left. In fact, when the object/limb does not have a perfectly cylindrical shape (which is the case of most limbs), such a measuring device according to the prior art, which nevertheless has a curvature defined between the opening and the connecting means, completely lacks in precision and the measurements are not reproducible. This is even more pronounced when the limb in question has a curvature that differs from that of the measuring element.

Moreover, since operators are not the same, measurements taken with such a measuring device are not reproducible; in the example of the wrist stated above, if the operator positions the device one way rather than another, entirely different measurements will be obtained.

It follows from all this that a currently used device is not versatile since it does not allow to obtain accurate and reproducible measurements of circumferences for all types of objects/limbs, each inevitably having a different circumference and curvature. Furthermore, as noted above, there are major problems of reproducibility of measurements, especially when different operators perform the circumference measurements on the same object/limb.

Document EP1 439 370 proposes a measuring device in which the exit opening is equipped with a connecting means in which the end of the measuring element can be inserted when it is wrapped around the limb to be measured.

Unfortunately, such a device is not reliable and not very practical, since the patient's skin can get trapped in the connecting means at the exit opening. This is particularly uncomfortable for the user. The accuracy of the measurement is also affected.

The invention aims to overcome the disadvantages of the prior art by providing a device for measuring the circumference of an object, particularly the circumference of a limb, which can ensure rapid, reliable, accurate and reproducible measurements for any type of object/limb, regardless of whether the latter has a small circumference (wrists, ankles, fingers, etc.) or a large circumference (abdomen, etc.) or one particular type of curvature/shape (e.g. due to the presence of a protuberance such as the wrist or ankle) instead of another.

Furthermore, the invention also aims to provide a measuring device of a reasonable size that is handy, light and compact so that it can be easily stowed in the pocket of a garment, which is also an advantage in the medical field where professionals in the health field have to keep moving from room to room or from one cabinet to another to examine their patients, and hence they frequently store their equipment in the pockets of their work smock.

In this sense, the present invention intends to provide a measuring device that is versatile and that is not limited to specific circumferences and/or objects or individual limbs, by ensuring that reproducible and reliable measurements are possible at a given location of the object/limb, irrespective of the positioning of the measuring device and regardless of the operator.

To solve this problem, the invention defines a device for measuring the circumference of an object as indicated at the beginning, characterized in that the said connecting means is located on the said at least one wall of the said winder, is adjacent to the said exit opening, is in the form of a protuberance that extends in the direction of the said distal end of the said measuring element, and is designed to receive the connecting element in a stationary manner, when the said measuring element is in the measuring position.

Unexpectedly in the context of this invention, it was determined that the presence of the connecting means allows guaranteeing the accuracy and ease of taking measurements, regardless of the type or shape of the object whose circumference is to be measured. Thus, the device according to the invention is resistant, durable and allows measuring the circumference of an object/limb rapidly, accurately, reproducibly and reliably, regardless of whether or not this object/limb has curvatures and/or protuberances, and regardless of the operator taking the measurement of the circumference.

Advantageously, the said distance d defined between the said exit opening and the said connecting means is equal to 5 mm, preferably equal to 4 mm, preferably equal to 3 mm, more preferably equal to 2 mm, and most preferably equal to 1 mm.

According to a preferred embodiment, the distance d is equal to zero, which means that the connecting means is joined and is therefore in contact with the exit opening of the winder. Such a relative positioning between the connecting means and the winder exit opening especially allows avoiding any errors and bias in the measurement of a circumference of an object/limb. For example, since the exit opening is delimited by four walls, it is planned according to the invention for the connecting means to be placed in direct contact with one of these walls, such that the distance d is zero or at least only a few millimetres at the most.

The terms "flexible", "flexible measuring element" or "measuring element made of a flexible material", within the meaning of the present invention, refer to a measuring element whose flexibility allows it to follow/surround the surface of the object or limb whose circumference is to be measured, closely and in contact with the said object/limb.

Preferably, according to the invention, the said loop formed around the said object, in particular around the said limb, is placed in a single plane passing through a median longitudinal axis defined along the said measuring element. Such positioning of the loop and thus the unwound portion of the measuring element according to the invention allows ensuring optimum accuracy of the measurement of the circumference. Indeed, any bias is minimized since the loop is positioned in a single plane.

Advantageously, according to the invention, the said winder of the said device is a spring winder optionally equipped with a locking system and/or a rewinding system of the said measuring element. During the use of a measuring device according to the invention, the locking system advantageously makes it possible, after unwinding at least a portion of the measuring element, to lock the latter in order to facilitate the positioning of the measuring element around the object/limb.

Furthermore, following the positioning of the measuring element around the object/limb and after connecting the distal portion of the measuring element to the connecting means according to the invention, the rewinding system of the measuring element allows an automatic and proper placement of the measuring element around the object/limb whose circumference is to be measured. Indeed, since the unwound portion of the measuring element is usually longer than the circumference to be actually measured, for reasons of ease of placement of the measuring device, it then becomes necessary to ensure that the measuring element closely follows the contour of the object/limb; this may be achieved according to the invention by a (automatic) rewinding system of the measuring element, in particular for the unwound portion of the measuring element. Of course, any type of suitable winder can fall within the scope of the present invention.

Advantageously, the said measuring device according to the invention comprises at least one tension sensor housed within the said winder to detect that the measuring element is tensed, in order to be able to measure the tension; the said tension is preferably linked to a weight of between 5 and 3000 g, preferably between 15 and 1500 g, more preferably between 15 and 1000 g, advantageously between 15 and 500 g, more advantageously between 15 and 150 g, and/or also comprising a motor housed in the winder in order to apply sufficient tension for a weight that is within one of the aforementioned ranges.

Preferably, according to the invention, the said measuring element of the said device may or may not have graduations. According to the present invention, it is planned, according to a first embodiment, that the measurement of the circumference is detected visually through these graduations on the measuring element. According to a second embodiment, this reading can be performed using a dial that digitally displays the measured circumference value, in which case graduations are not necessary.

Preferably, according to the invention, the said exit opening of the said winder has a section similar to the section of the said measuring element. In this way, the exit opening guides the measuring element such that the latter can be affixed correctly around the object/limb whose circumference is measured. In particular, the fact that these two sections are similar allows the loop formed around the object/limb to be placed even better in a single plane passing through a median longitudinal axis defined on the measuring element. Within the meaning of the invention, the smaller the width of the measuring element, the more the measurement is reliable, accurate and reproducible, especially by minimizing the gap of the measuring element observed at the front side of the forearm, at the leg or at the calf.

Advantageously, according to the invention, the said measuring element of the said device is made of a flexible material such as flexible plastic or paper having sufficient tensile strength.

Advantageously, according to the invention, the said connecting means of the said device is connected to a mobile element designed to allow a movement of the said connecting means according to the said distance d defined between the said exit opening and the said connecting means. It is therefore possible, according to the invention, to vary the position of the connecting means, which may prove advantageous for taking certain types of measurements. The ability to move the connecting means allows adapting to the specific curvature of a given limb, regardless of whether or not the device according to the invention itself has a curvature.

Preferably, the said device according to the invention has a window used to read the circumference of an object, especially the circumference of a limb. Optionally, the reading window is combined with a magnifying glass to permit easier reading of graduations.

Preferably, according to the invention, the said distal end of the said measuring element of the said device is equipped with a connecting element that cooperates with the said connecting means such that it ensures a connection between the said connecting means and the said distal end of the said measuring element. Such a connection may be made via a male-female system enabling, for example, an interlocking of the connecting element present at the distal part of the measuring element in the connecting means. It is obvious that any other type of system or device capable of providing such a connection is an integral part of the present invention, such as a magnet fastener or a Velcro® fastener.

Advantageously, according to the invention, the said measuring element of the said device comprises an attachment area designed to be connected via a slide to a second measuring element having a longitudinal direction and defining a slide designed to be affixed along the length of an object, in particular along the length of a limb, the said slide having a slide passage opening delimited by four walls, of which at least two are parallel to each other and form a guide wall for the said slide, so as to insert the said measuring element in a plane perpendicular to the said longitudinal direction. For example, a measuring device according to the invention may be part of a measuring device such as the one disclosed in document WO2014/191513. In particular, a measuring device according to the invention can advantageously replace a measuring element such as the one referred to as the "second graduated measuring element" in document WO2014/191513.

Preferably, the measuring device according to the invention further comprises:
- an electronic measuring module capable of determining a circumference measurement from the unwinding of the said flexible measuring element; and
- display means for displaying a circumference measurement determined by the said electronic module.

This embodiment has the advantage of being able to perform a measurement quickly: the display means allow the operator to directly read a circumference measurement. The use of an electronic module capable of determining a circumference measurement also provides better reproducibility of the measurement of the circumference of an object, in particular the circumference of a limb, because variations due to operator intervention are significantly limited by the automation/digitalization of the measuring device. The reading of the measurement is also easier because the circumference value is displayed through the display means.

Preferably, the measuring device according to the invention further comprises communication means for communicating a circumference measurement determined by the said electronic module to another electronic device. This communication of the measuring device with another electronic device through the communication means advantageously helps, for example, the person performing the circumference measurement to skip transcribing the measurement displayed by the display means.

Preferably, the measuring device according to the invention further comprises control means for controlling a transmission of a circumference determined by the said electronic module by the communication means. The advantage of having control means built into the measuring device is that the operator can determine when he wishes the circumference measurement to be communicated, preferably to the display means and preferably to the communication means so that the measurement can be communicated to another electronic device.

Advantageously, the device according to the invention comprises the said tension sensor and/or a motor, in which a tensile force can be programmed and a signal warns the user when this tensile force is achieved. This helps to sufficiently tighten the measuring element around the object/limb whose circumference is to be measured or examined. This is particularly advantageous for practitioners such as surgical truss makers who have to be able to apply sufficient tension to take a reliable, accurate and reproducible measurement or examination.

The said motor may preferably be replaced by a pressure gauge in which the tensile force can be programmed, such that once the predefined pressure is achieved, the device emits an audio signal.

A motor shall be preferred for bearing weights between 5 and 80 g, preferably between 5 and 60 g.

A motor shall be preferred for bearing weights of more than 80 g and less than 5 kg.

Other embodiments of a device according to the invention are indicated in the appended claims.

The present invention also relates to an assembly comprising the measuring device according to the invention and an apparatus capable of communicating with the said communication means of the said measuring device. The advantage of this assembly is, on an apparatus capable of communicating with the said communication means, to obtain the circumference measurement without having to transcribe the measurement and thus to avoid reading and input errors.

Preferably, the assembly according to the invention is characterized in that:
  the said apparatus comprises a memory comprising data for defining a position on the said slide, in that
  the said apparatus is able to communicate with the said communication means of the said measuring device for transmitting the said data used to define a position on the slide, and in that
  the said display means are able to display the said data for indicating one or more positions on the slide to a user.

The advantage of this embodiment is that the measuring device, via the display means, can indicate the location where the measurement must be taken to the operator taking the measurement. This allows taking measurements faster. This also allows taking multiple measurements on the same object or the same limb at intervals that are indicated by the apparatus to the display means of the measuring device and which are therefore transmitted to the operator. The operator thus has all the information concerning the measurement that he has to take. This provides a better pace of measurement and improved reliability of the measurements. The measurement and the scrolling of the location where the measurement is to be taken are controlled through the control means.

Further embodiments of an assembly according to the invention are indicated in the appended claims.

The present invention also relates to a use of a device or an assembly according to the invention for measuring the circumference of an object, especially for measuring the circumference of a limb.

Other forms of use of a device or an assembly according to the invention are indicated in the appended claims.

Other features, details and advantages of the invention will emerge from the description given below, without limitation and with reference to the accompanying drawings.

In the figures, identical or similar elements bear the same references.

Figure 1:
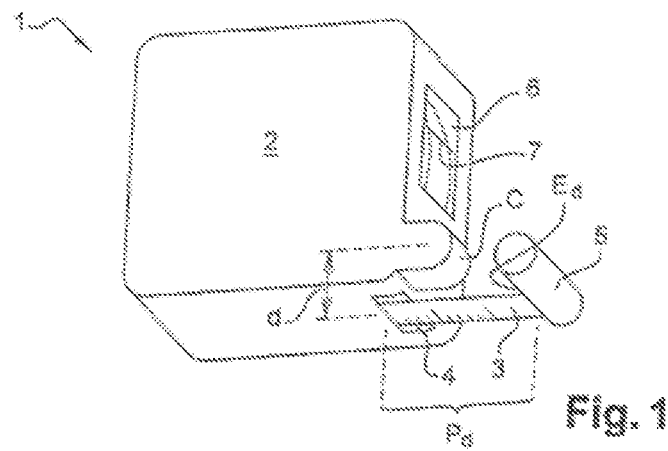
FIG. 1 is a schematic representation of a first embodiment of a measuring device according to the invention.

FIG. 1 illustrates a measuring device 1 for measuring the circumference of an object, in particular the circumference of a limb. The measuring device 1 comprises:
  a winder 2 (for example, a spring winder 2) designed to wind and unwind a measuring element 3 in the form of a tape made of a flexible material, the winder further having an exit opening 4 designed to allow the exit of at least one unwound portion $P_d$ of the measuring element 3, this unwound portion $P_d$ being defined between the exit opening 4 and the distal end $E_d$ of measuring element 3; and
  connecting means C of the distal end $E_d$ of the measuring element 3, these connecting means C being located at a distance d from the exit opening 4 of the winder 2. As illustrated, the winder 2 has a reading window 6 comprising a marker 7 where the circumference can be read.

Figure 2:
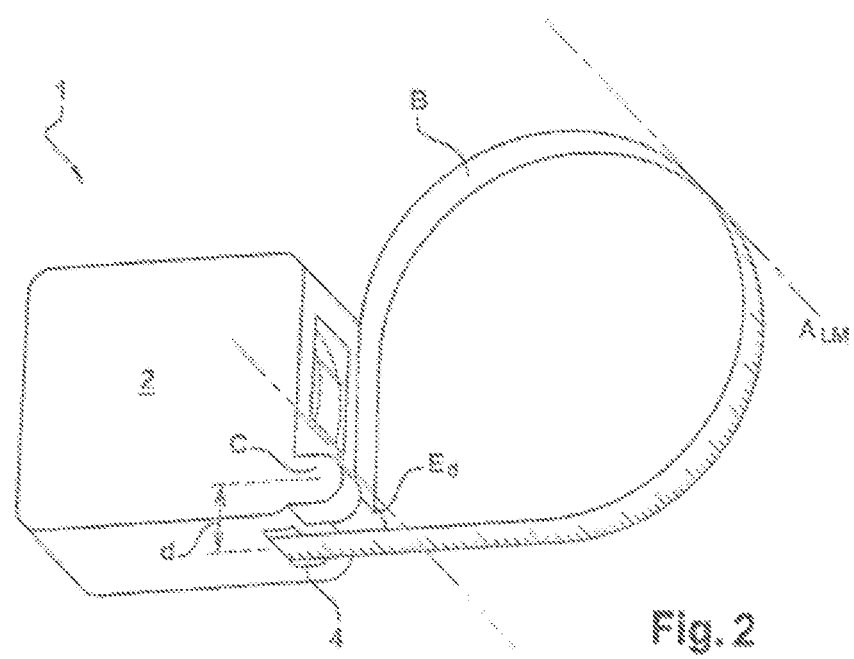
FIG. 2 is a schematic representation corresponding to the first embodiment of a measuring device according to FIG. 1, where the measuring element forms a loop.

FIG. 2 is a schematic representation corresponding to the first embodiment of a measuring device 1 according to FIG. 1, where the measuring element 3 forms a loop B. As illustrated, when the distal end $E_d$ of the measuring element 3 is connected using the connecting means C, the unwound portion $P_d$ of the measuring element 3 forms a loop B that, preferably, is placed in a single plane passing through a median longitudinal axis $A_{LM}$ defined along the measuring element 3. This connection is achieved by interlocking a connecting element 5 present at the distal end $E_d$ of the measuring element 3 in the connecting means C.

Moreover, as also illustrated, the winder 2 has a reading window 6 for reading the circumference of the object/limb measured, where the operator can determine the value (typically in centimetres and millimetres) of the measured circumference.

Advantageously, a measuring device 1 as illustrated in FIG. 1 and in FIG. 2 also comprises a locking system (not shown) and a rewinding system, for example one that uses a motor or a spring (not shown), of the measuring element 3. For example, these systems can be operated by a button located on winder 2.

Figure 3:
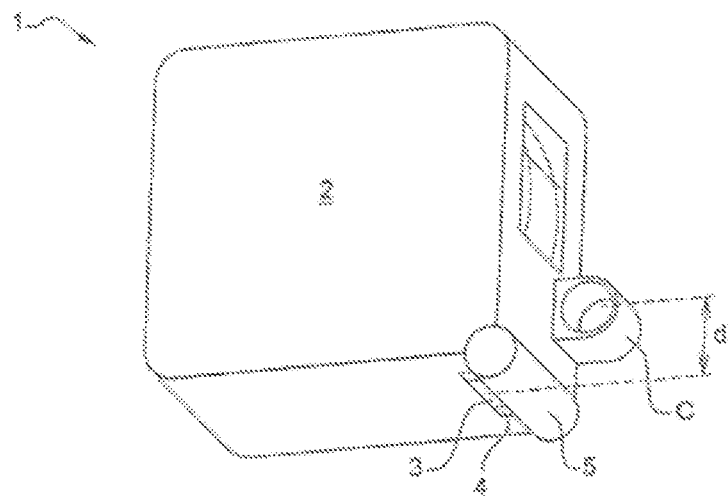
FIG. 3 is a schematic representation of another embodiment of a measuring device according to the invention.

FIG. 3 illustrates another measuring device 1 for measuring the circumference of an object, in particular the circumference of a limb. This measuring device 1 according to FIG. 3 includes the same elements as those shown in FIG. 1, but the connecting means C and the exit opening 4 of the winder 2 are further apart from one another at a distance d of less than or equal to 4 cm, preferably less than or equal to 3 cm, preferably less than or equal to 2 cm, more preferably less than or equal to 1 cm.

Figure 4:
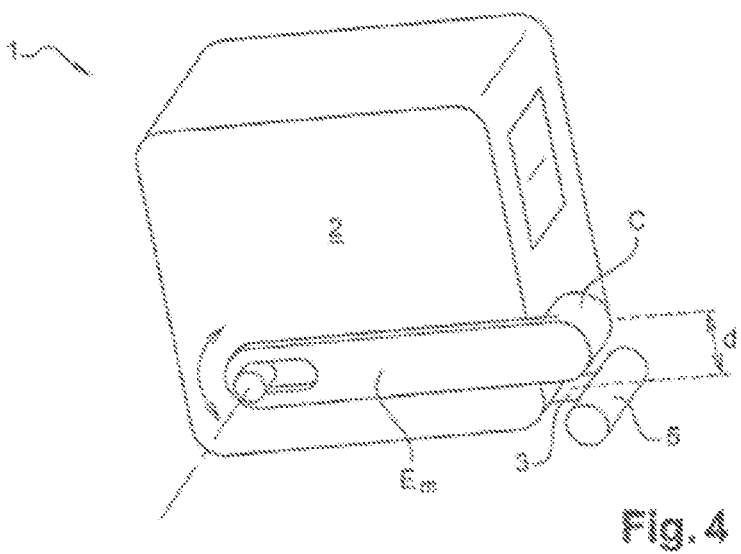
FIG. 4 is a schematic representation of yet another embodiment of a measuring device according to the invention.

FIG. 4 illustrates yet another measuring device 1 for measuring of the circumference of an object, in particular the circumference of a limb. This measuring device 1 according to FIG. 3 comprises the same elements as those shown in FIG. 1, but the connecting means C is connected to a mobile element $E_m$ designed to permit the movement of the connecting means C (as indicated by the double arrow) at distance d defined between the said exit opening 4 and the said connecting means C, i.e. at a distance d of less than or equal to 4 cm, preferably less than or equal to 3 cm, preferably less than or equal to 2 cm, more preferably less than or equal to 1 cm.

Figure 5:
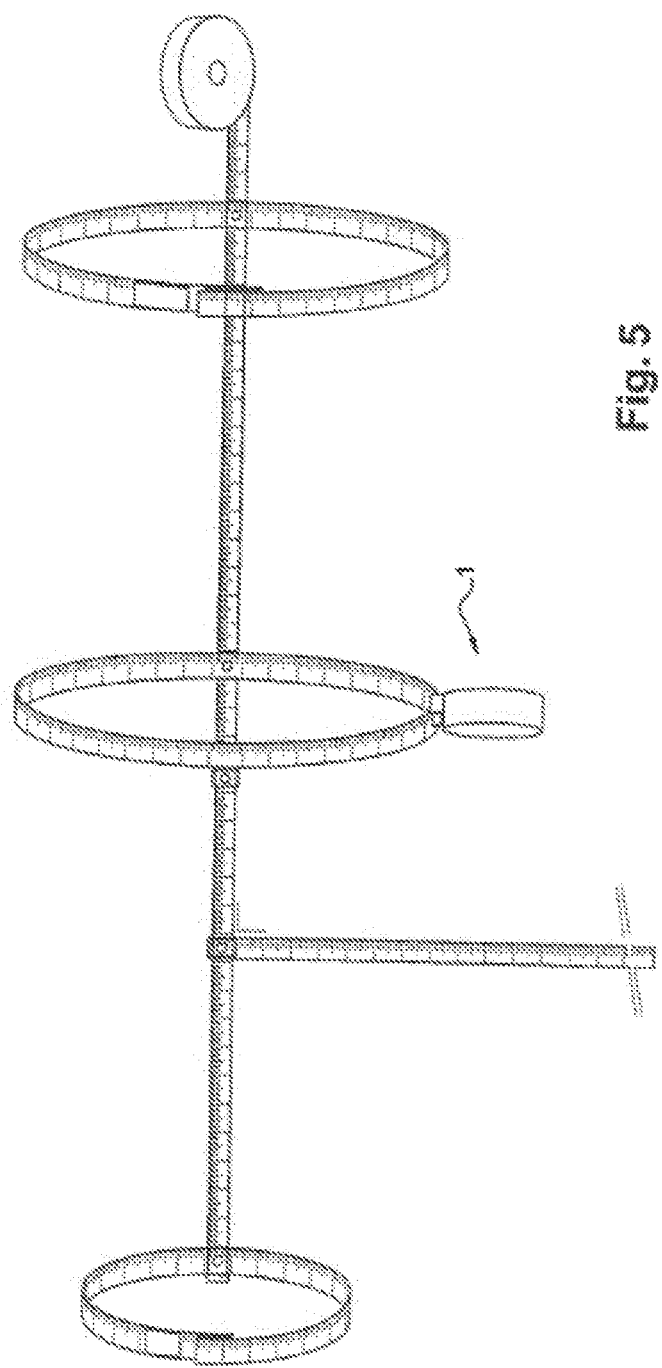
FIG. 5 illustrates a measuring device according to the invention, which is connected to an iterative device for measuring the circumference of an object/limb, for example an iterative measuring device according to document WO2014/191513.

FIG. 5 shows a measuring device 1 according to the invention, connected to an iterative device for measuring the circumference of an object/limb, such as the iterative measuring device according to document WO2014/191513.

EXAMPLE

In order to validate the measuring device according to the invention, several measurements were made at different parts of the bodies of two patients. As indicated in the table below, the following measuring devices were compared:
measuring device according to the invention where the distance d defined between the exit opening and the said connecting means is 0.5 cm;
measuring device of the prior art where the distance d defined between the exit opening and the said connecting means is equal to 5.5 cm;
a conventional measure (tape measure) as a reference (control).

Measurements were taken at the index finger (above and to the side), at the wrist when the device is positioned just behind the head of the ulna (like a wristwatch), at the wrist when the device is offset by 90° with respect to the position just behind the head of the ulna, at the ankle when the device is positioned above the malleolus and at the ankle when the device is offset by 90° with respect to the previous position.

The results obtained during these measurements are presented in Table 1 below. In this Table, the measurements relating to the first individual are in "normal" font while the measurements of the second individual are shown in italics.

TABLE 1

| | Wrist | | Finger (index) | | Ankle | |
|---|---|---|---|---|---|---|
| | Like a wristwatch | Offset by 90° | On top of the finger | Offset by 90° | Above the malleolus | Offset by 90° |
| Tape measure: control | 14.5 cm 17.2 cm | 14.5 cm 17 cm | 4.8 cm 5.5 cm | 4.8 cm 5.5 cm | 21.2 cm 22.3 cm | 21.3 cm 22.3 cm |
| Current device | 16.3 cm 18 cm | 17.2 cm 19.4 cm | 11 cm 11 cm | 11 cm 11 cm | 22.4 cm 23.3 cm | 21.3 cm 22.2 cm |
| Device as per the invention | 14.5 cm 17 cm | 14.5 cm 17 cm | 4.6 cm 5.5 cm | 4.6 cm 5.5 cm | 21.1 cm 22.1 cm | 21.1 cm 22.2 cm |

As can be seen, with a device according to the invention, for each individual and each limb considered, only a difference of 1 to 2 mm is observed compared to the measurements taken with the control (tape measure). This proves that a device according to the invention enables taking reliable measurements regardless of the positioning of the measuring device on the limb in question.

On the contrary, with a device of the prior art (current device), measurement differences of several centimetres (up to 6 cm in the case of measuring the circumference of an index finger) are observed with respect to the control. As can be seen, the smaller/thinner the limb, the more erroneous and biased the measurement is when using a measuring device according to the prior art, but not when using a device according to the invention, which is versatile and allows taking measurements that are not only reliable but also reproducible.

It is understood that this invention is in no way limited to the embodiments described above and that many modifications may be made without departing from the scope of the appended claims.

The invention claimed is:

1. A measuring device for measuring the circumference a limb or other object, the measuring device comprising:
    a winder of a flexible first measuring element designed to be affixed and form a loop around the limb or other object when the first measuring element is in a measuring position, the winder having at least one wall and an exit opening designed to allow an exit of at least one unwound portion of the first measuring element, the at least one unwound portion of the first measuring element defined between the exit opening and a distal end of the first measuring element, the distal end of the first measuring element equipped with a connecting element that abuts against the exit opening when the first measuring element is in a resting position; and
    connecting means of the connecting element of the distal end of the first measuring element, the connecting means located at a distance d from the exit opening, the distance d defined between the exit opening and the connecting means being less than or equal to 4 cm,
    wherein the connecting means is located on the at least one wall of the winder, is adjacent to the exit opening, is in the form of a protuberance, which extends in the direction of the distal end of the first measuring element, and is designed to fit, in a stationary manner, with the connecting element, when the first measuring element is in the measuring position, and
    wherein the first measuring element has an attachment area designed to be connected via a slider to a second measuring element with a longitudinal direction and defining a slide designed to be affixed along the length of the limb or other object, the slider having a slide passage opening delimited by four walls, of which at least two of the walls are parallel to each other and form a guide wall for the slider to position the first measuring element in a plane perpendicular to the longitudinal direction.

2. The measuring device according to claim 1, wherein the loop formed around the limb or other object is placed in a single plane passing through a median longitudinal axis defined along the length of the first measuring element.

3. The measuring device according to claim 1, wherein the winder is a spring winder equipped with a locking system and/or a rewinding system of the first measuring element.

4. The measuring device according to claim 1, wherein the first measuring element has graduations.

5. The measuring device according to claim 1, wherein the exit opening of the winder has a section similar to the section of the first measuring element.

6. The measuring device according to claim 1, wherein the first measuring element is made of at least one of a flexible material, a flexible plastic, or paper.

7. The measuring device according to claim 1, further including a window for reading the circumference of the limb or other object.

8. The measuring device according to claim 1, further including:

an electronic measuring module to determine a circumference measurement using the unwinding of the flexible measuring element; and display means for displaying a circumference measurement determined by the electronic module.

9. The measuring device according to claim 8, further including communication means for communicating a circumference measurement determined by the electronic module to another electronic device.

10. The measuring device according to claim 9, further including control means for controlling a transmission of a circumference determined by the electronic module via the communication means.

11. An assembly comprising:
the measuring device according to claim 1; and
an apparatus capable of communicating with the communication means of the measuring device.

12. An assembly comprising:
the measuring device of claim 1:
an apparatus capable of communicating with the communication means of the measuring device, wherein:
the apparatus comprises a memory comprising data that enables defining one or more positions on the slide,
the apparatus is able to communicate with the communication means of the measuring device to transmit the data for defining the one or more positions on the slide; and
display means to display the data to indicate the one or more positions on the slide to a user.

13. The measuring device according to claim 1, wherein the distance d defined between the exit opening and the connecting means is less than or equal to 3 cm.

14. The measuring device according to claim 1, wherein the distance d defined between the exit opening and the connecting means is less than or equal to 2 cm.

15. The measuring device according to claim 1, wherein the distance d defined between the exit opening and the connecting means is less than or equal to 1 cm.

16. The measuring device according to claim 1, wherein the distance d defined between the exit opening and the connecting means is zero.

17. A device for measuring the circumference of a limb or other object, the device comprising:
a winder of a flexible measuring element designed to be affixed and form a loop around the limb or other object when the measuring element is in a measuring position, the winder having at least one wall and an exit opening designed to allow an exit of at least one unwound portion of the measuring element, the at least one unwound portion of the measuring element defined between the exit opening and a distal end of the measuring element, the distal end of the measuring element equipped with a connecting element that abuts against the exit opening when the measuring element is in a resting position;

connecting means of the connecting element of the distal end of the measuring element, the connecting means located at a distance d from the exit opening, the distance d defined between the exit opening and the connecting means being less than or equal to 4 cm, wherein the connecting means is located on the at least one wall of the winder, is adjacent to the exit opening, is in the form of a protuberance, which extends in the direction of the distal end of the measuring element, and is designed to fit, in a stationary manner, with the connecting element, when the measuring element is in the measuring position; and at least one of: (1) at least one tension sensor housed in the winder to detect when the measuring element is tensed and to be able to measure the tension, or (2) a motor housed in the winder to apply the tension, the tension being linked to at least one of: (a) a weight between 5 and 3000 g, (b) a weight between 15 and 1500 g, (c) a weight between 15 and 1000 g, (d) a weight between 15 and 500 g, or (e) a weight between 15 and 150 g.

18. A device for measuring the circumference of a limb, the device comprising:
a winder of a flexible measuring element designed to be affixed and form a loop around the limb when the measuring element is in a measuring position, the winder having at least one wall and an exit opening designed to allow an exit of at least one unwound portion of the measuring element, the at least one unwound portion of the measuring element defined between the exit opening and a distal end of the measuring element, the distal end of the measuring element equipped with a connecting element that abuts against the exit opening when the measuring element is in a resting position; and connecting means of the connecting element of the distal end of the measuring element, the connecting means located at a distance d from the exit opening, the distance d defined between the exit opening and the connecting means being less than or equal to 4 cm, wherein the connecting means is located on the at least one wall of the winder, is adjacent to the exit opening, is in the form of a protuberance, which extends in the direction of the distal end of the measuring element, and is designed to fit, in a stationary manner, with the connecting element when the measuring element is in the measuring position, and wherein the connecting means is connected to a mobile element ($E_m$) designed to permit movement of the connecting means along the distance d defined between the exit opening and the connecting means.

* * * * *